(12) United States Patent
Kato

(10) Patent No.: US 10,251,730 B2
(45) Date of Patent: Apr. 9, 2019

(54) IMPLANT BODY

(71) Applicant: IMPLANT AND TISSUE ENGINEERING DENTAL NETWORK-TOKYO, LIMITED CO., Tokyo (JP)

(72) Inventor: Eiji Kato, Tokyo (JP)

(73) Assignee: IMPLANT AND TISSUE ENGINEERING DENTAL NETWORK-TOKYO, LIMITED CO, Tokyo (JP)

( * ) Notice: Subject to any disclaimer, the term of this patent is extended or adjusted under 35 U.S.C. 154(b) by 116 days.

(21) Appl. No.: 15/120,194

(22) PCT Filed: Feb. 18, 2015

(86) PCT No.: PCT/JP2015/054367
§ 371 (c)(1),
(2) Date: Aug. 19, 2016

(87) PCT Pub. No.: WO2015/125799
PCT Pub. Date: Aug. 27, 2015

(65) Prior Publication Data
US 2017/0056133 A1 Mar. 2, 2017

(30) Foreign Application Priority Data

Feb. 21, 2014 (JP) .................... 2014-031290

(51) Int. Cl.
*A61L 27/04* (2006.01)
*A61L 27/10* (2006.01)
(Continued)

(52) U.S. Cl.
CPC .......... *A61C 8/0013* (2013.01); *A61C 8/0012* (2013.01); *A61C 8/0015* (2013.01);
(Continued)

(58) Field of Classification Search
CPC ... A61C 8/0012; A61C 8/0013; A61C 8/0015; A61C 2008/0046; A61K 6/0205;
(Continued)

(56) References Cited

U.S. PATENT DOCUMENTS

2004/0267376 A1* 12/2004 Suzuki .................... A61L 27/10
623/23.5
2005/0031663 A1 2/2005 Larsson et al.
(Continued)

FOREIGN PATENT DOCUMENTS

EP 1 095 760 5/2001
JP 6-125978 5/1997
(Continued)

OTHER PUBLICATIONS

Search Report issued in International Bureau of WIPO Patent Application No. PCT/JP2015/054367, dated Mar. 31, 2015.

*Primary Examiner* — Laura A Auer
(74) *Attorney, Agent, or Firm* — Greenblum & Bernstein, P.L.C.

(57) ABSTRACT

The present invention provides an implant body formed from metal or ceramics as a raw material, the implant body including a modified surface, provided with a plurality of projections and a plurality of crevasse-like nanoscale grooves, by which focal adhesion formation, penetration of collagen fibers, arrangement of the collagen fibers in a single direction to thereby adhere to connective tissue, and soft tissue sealablity are possible. According to such a surface modification, focal adhesion formation and the arrangement of the cell cytoskeleton can be enhanced, and penetration of collagen fibers into the surface internal portion is possible.

2 Claims, 19 Drawing Sheets

(51) Int. Cl.
*A61C 8/00* (2006.01)
*A61K 6/02* (2006.01)
*A61K 6/04* (2006.01)
*A61K 6/00* (2006.01)

(52) U.S. Cl.
CPC .......... *A61K 6/0038* (2013.01); *A61K 6/0044* (2013.01); *A61K 6/0205* (2013.01); *A61K 6/04* (2013.01); *A61L 27/04* (2013.01); *A61L 27/10* (2013.01); *A61C 2008/0046* (2013.01); *A61L 2400/12* (2013.01); *A61L 2400/18* (2013.01)

(58) Field of Classification Search
CPC ...... A61K 6/04; A61K 6/0044; A61K 6/0038; A61L 27/10; A61L 27/04; A61L 2400/18
See application file for complete search history.

(56) References Cited

U.S. PATENT DOCUMENTS

| | | | |
|---|---|---|---|
| 2009/0220561 A1 | 9/2009 | Jin et al. | |
| 2010/0268330 A1 | 10/2010 | Tong et al. | |
| 2010/0268346 A1 | 10/2010 | Tong et al. | |
| 2010/0268347 A1 | 10/2010 | Tong et al. | |
| 2011/0033661 A1 | 2/2011 | Oawa | |
| 2011/0059312 A1 | 3/2011 | Graeme et al. | |
| 2011/0125263 A1 | 5/2011 | Webster et al. | |
| 2011/0190902 A1 | 8/2011 | Tong et al. | |
| 2012/0183923 A1 | 7/2012 | Takagi et al. | |
| 2013/0013082 A1 | 1/2013 | Ishiai et al. | |

FOREIGN PATENT DOCUMENTS

| | | |
|---|---|---|
| JP | 2001-149061 | 6/2001 |
| JP | 2002-511782 | 4/2002 |
| JP | 2005-34333 | 2/2005 |
| JP | 2008-538515 | 10/2008 |
| JP | 2010-246927 | 11/2010 |
| JP | 2010-246928 | 11/2010 |
| JP | 2010-536451 | 12/2010 |
| JP | 2010-536534 | 12/2010 |
| JP | 2011-156360 | 8/2011 |
| JP | 4804648 | 8/2011 |
| JP | 2011-194099 | 10/2011 |
| JP | 2012-143416 | 8/2012 |

\* cited by examiner

Alkali-heated (AH) with 5M NaOH

Alkali-heated (AH) with 10M NaOH

IMPLANT BODY

TECHNICAL FIELD

The present invention relates to an implant body used in an artificial dental root or to an implant body which is applicable to a penetration implant that penetrates both the mucosa and the dermal tissue, and in particular, relates to an implant body which has been subject to surface modification for soft tissue sealing.

BACKGROUND ART

In the field of dentistry, a treatment method for rebuilding a missing part of a dentition after dental extraction is known in which a dental implant, such as an artificial dental root, etc., is inserted into body tissue, to be used as a substitute for the missing part.

During this treatment, due to bone tissue being formed around the embedding location of the implant, which embeds the missing part of the bone, etc., it is important to favorably form the bone tissue to be in physically intimate contact (osseointegration) with the implant and the bone without fiber tissue between them, and hence, an artificial dental root which binds with the bone is used.

For example, Patent Literature No. 1, indicated below, discloses an invention related to a bone substitute material formed of titanium or a titanium alloy.

According to Patent Literature No. 1, long term and stable osteocompatibility can be obtained by adjusting the alkali metal density of the osteocompatible-coated surface between 0.8 at. % and 3.2 at. %.

CITATION LIST

Patent Literature

[Patent Literature No. 1] Japanese Patent No. 4,804,648

SUMMARY OF INVENTION

Technical Problem

As described above, in Patent Literature No. 1, the alkali metal density of the osteocompatible-coated surface is adjusted in order to improve osteocompatibility with respect to the bone; however, in addition to binding with the bone, there has also been a need for the adhering of the transmucosal part of the implant to soft tissue fibers formed from strong collagen molecules as a biological barrier for shutting out the pathway of oral bacteria, which is the cause of infection of tissue around the implant, in order to achieve clinical long-term stability.

The present invention has been devised with consideration of the above problems, and it is an objective to provide an implant body used in an artificial dental root or to an implant body which is applicable to a penetration implant that penetrates both the mucosa and the dermal tissue, and in particular, relates to an implant body to which surface modification has been carried out for soft tissue sealing.

Solution to Problem

The biological sealing around the periodontal (gingival) tissue is dependent on not only the adherence to the epidermis, but also on the adherence to the dental root surface of the connective tissue by mainly a fiber structure that binds the dental root to the gum. This fiber structure is configured of gingival fibers and Sharpey's fibers. Specifically, collagen fibers having a diameter of approximately 70 nm form a collagen fiber bundle, having a diameter of a few micrometers, and are inserted as Sharpey's fibers into, and adhered to, the cementum of the dental root surface from the alveolar bone. The gingival fibers (collagen fibers) are vertically oriented with respect to the cementum of the dental root surface from the upper periodontal internal portion of the alveolar bone and are adhered thereto. These Sharpey's fibers and gingival fibers firmly fasten the connective tissue between the dental root and the alveolar bone, and provide a resistive force against inflammation of the gingiva and gingival tissue, and against mechanical stress.

Whereas, an artificial dental root that constitutes a dental implant conventionally cannot obtain direct adherence between the implant surface and the gingival connective tissue, which is formed from collagen fibers such as Sharpey's fibers and gingival fibers, so that since no sealablity can be provided by the soft tissue around the implant, this becomes the cause of infection and inflammation.

Consequently, as a result of diligent research carried out by the inventor of the present invention in order to solve the above-described problems, the inventor was able to achieve an adherence effect with respect to the connective tissue and achieve an improvement in the sealablity of the soft tissue by modifying the implant surface. Specifically, the present invention is indicated hereinbelow.

In the present invention, an implant body formed from metal or ceramics is provided, the implant body including a modified surface, provided with a plurality of projections and a plurality of crevasse-like nanoscale grooves, by which focal adhesion formation, penetration of collagen fibers, arrangement of the collagen fibers in a single direction to thereby adhere to connective tissue, and soft tissue sealablity are possible.

In the present invention, an implant body formed from metal or ceramics is provided, the implant body including a modified surface having soft tissue sealablity, and which is formed at a size that prevents entrapment of bacteria.

In the present invention, an implant body formed from metal or ceramics is provided, wherein, with respect to an SEM image, the average number of projections occupying 1 square μm is 20 through 60; the average area of the projections occupying 1 square μm is 0.25 μm$^2$ through 0.40 μm$^2$; the average groove width of the crevasse-like grooves is 0.15 μm through 0.30 μm; the average value of Ra in 120 square μm is 0.15 μm through 0.50 μm; and the average value of Rsm in 120 square μm is 1.50 μm through 3.00 μm.

In the implant body of the present invention, surface modification has been carried out so that cell adhesion and focal adhesion formation are enhanced in both the epidermis and the mucosal epithelium.

In the implant body of the present invention, the implant body can be applied to a penetration implant that penetrates both the mucosa and the dermal tissue.

Advantageous Effects of Invention

According to the implant body of the present invention, a configuration having adherence ability with connective tissue can be provided, thereby obtaining an adherence effect between the connective tissue and the implant surface, and improving sealablity of the soft tissue.

BRIEF DESCRIPTION OF DRAWINGS

FIG.

FIG. 17A shows an SEM photograph of the titanium substrate of Comparative Example (5M-AH), and FIG. 17B shows an SEM photograph of the titanium substrate of Present Example (10M-AH).

DESCRIPTION OF EMBODIMENTS

Figure 1:
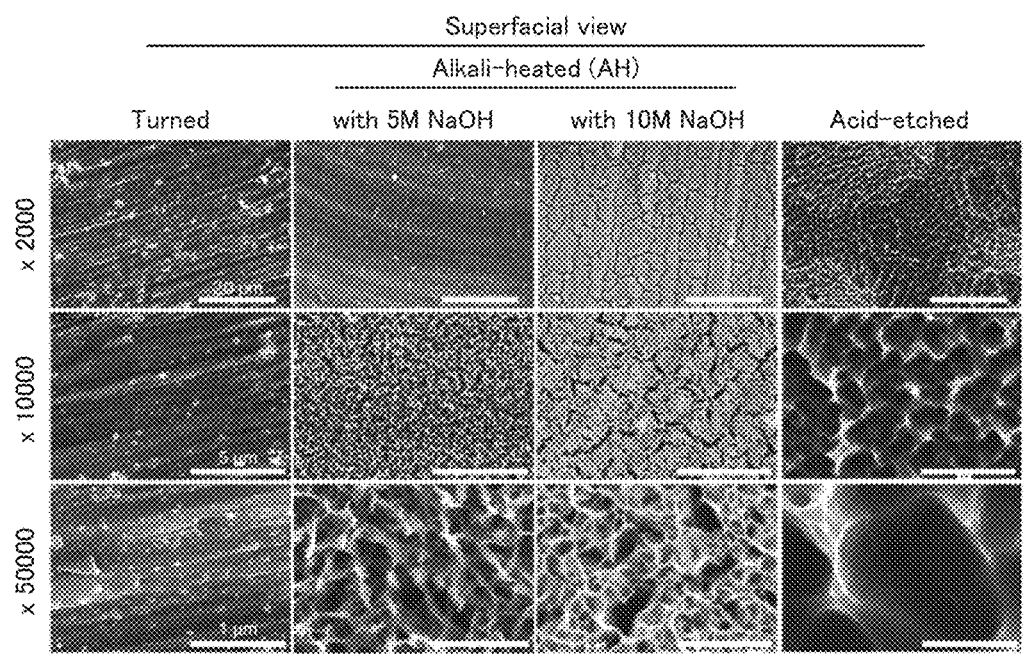
FIG. 1 are SEM photographs of surface views of surface processes carried out on a titanium substrate, showing the case of being turned using a lathe, treated with 5M NaOH, 10M NaOH, and being etched (acid-etched).

In the present invention, an implant body, formed from metal or ceramics as a raw material, is subject to surface modification; the surface modification having a plurality of projections and nano-grooves that are defined by a plurality of crevasses. In the present invention, crevasse grooves which are formed as cracks in the implant surface have been confirmed. Furthermore, a large number of projections that protrude from the surface portion, other than at the grooves, have also been confirmed. Whereas, in a conventional implant body, grooves having the shape of crevasses like those of the present invention are not confirmed.

In the present invention, the average number of projections occupying 1 square micrometer, the average area of the projections occupying 1 square micrometer, the average groove width of crevasse-like grooves, the average value of Ra per 120 square micrometers, and the average value of Rsm per 120 square micrometers have been specified, respectively. By specifying the scope of each parameter, an adhesion effect between the gingival connective tissue and the implant surface can be obtained.

It is concluded that the projections that protrude from the implant surface promote the focal adhesion of gingival fibroblastic cells and the arrangement of the cell cytoskeleton. Accordingly, cell adhesion strength can be improved and the intracellular signal transduction pathway, starting from the cell cytoskeleton, can be activated, thereupon resulting in improvement in the manifestation of gingival collagen fiber production. Furthermore, the produced collagen fibers entangle with the projections and penetrate the implant surface from the crevasse-like grooves, so that a Sharpey's fiber structure is formed on the implant surface. In addition, if the large number of projections are arranged at regular intervals without concentrating at one location, cellular extension and cellular proliferation are enhanced. Accordingly, exceeding the general cell biological rule that says "cell differentiation capacity and cell proliferation capability have an inverse proportional relationship", it is concluded that both the matrix production was improved while maintaining the cell proliferation capability.

Furthermore, in the present invention, the crevasse-like grooves are nano-scale, are smaller than bacteria so that entrapment of bacteria does not easily occur.

As discussed later, the average number of projections occupying 1 square micrometer, the average area of the projections occupying 1 square micrometer, and the average value of Ra per 120 square micrometers of the present invention are all greater compared to those of the Comparative Example. Accordingly, in the present invention, compared to the Comparative Example, the cell adhesive strength is improved and entanglement of the produced collagen fibers starts to occur. Furthermore, in the present invention, the average groove width of the crevasse-like grooves is larger compared to those of the Comparative Example. Accordingly, in the present invention, compared to the Comparative Example, it is easier for the grown collagen fibers to be inserted deeper into the grooves, and since Rsm is greater, the matrix production capability of the gingival fibroblastic cells is improved while further enhancing cellular extension and cellular proliferation.

Accordingly, the implant body of the present invention can have a configuration that has connective-tissue adhesiveness, thereby achieving an adhesion effect between connective tissue and the implant surface, and improving the soft tissue sealablity.

It is possible to apply the present invention to a skin-penetration endosseous implant (endosseous fastener) other than at the dental and oral mucosal region, or to various skin-penetration medical devices such as a gastrostoma, a tracheostomy insertion tube, artificial vocal cords, and a blood vessel indwelling needle, etc. (central venous nutrition indwelling needle, etc.). Accordingly, the present invention is applicable to a penetration implant that penetrates both the mucosa and the dermal tissue, thereby promoting cell adhesion and focal adhesion formation in both the epidermis and the mucosal epithelium.

The following processes were carried out on a substrate formed of titanium (Ti) (hereinafter, "titanium substrate").

A: Lathe Turning

A substrate that is a cross section of a titanium bar cut off with an electric saw, and is turned and polished using a lathe machine.

B: 5M NaOH Treatment

A machine-polished titanium substrate was immersed in 5M NaOH aqueous solution under the conditions of 60° C. for 24 hours, and thereafter, a heating process was carried out on the titanium substrate at 600° C. for 1 hour.

C: 10M NaOH Treatment

A machine-polished titanium substrate was immersed in 10M NaOH aqueous solution under the conditions of 90° C. for 24 hours, and thereafter, a heating process was carried out on the titanium substrate at 600° C. for 1 hour.

It should be noted that before the NaOH treatment was carried out, ultrasonication in the order of acetone, ethanol and ultrapure water, and short wavelength ultra-violet irradiation was performed in order to remove as much organic material from the surface as possible. By carrying out ultrasonication and ultra-violet irradiation in such a manner, the hydrophily of the titanium surface can be improved, and has a favorable wetness with respect to an alkali aqueous solution.

Furthermore, after the immersion in the alkali aqueous solution, ultrasonication is carried out before heat treatment is carried out at 600° C., and after the heat treatment is carried out at 600° C., ultrasonication is carried out in ultrapure water, and upon drying, ultra-violet irradiation is carried out.

D: Acid Etching

The titanium substrate was heated to 120° C. and immersed into a 70% hot sulfuric acid solution for 75 seconds, and thereafter washed in distilled water.

Figure 2:
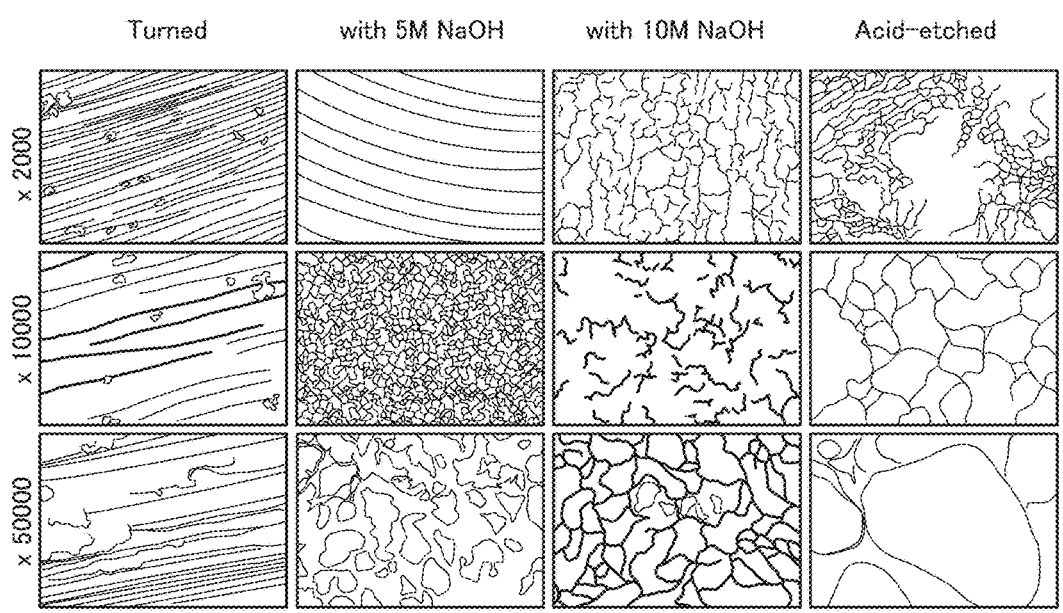
FIG. 2 shows partial schematic views of the SEM photographs shown in FIG. 1.

Subsequently, SEM photographs of the surfaces of the titanium substrates that were processed/treated in the above-described manner were observed. The test results thereof are shown in FIG. 1. Furthermore, FIG. 2 shows partially schematic diagrams of the SEM photographs that are shown in FIG. 1.

FIG. 1 shows the SEM photographs of the observed surfaces the titanium substrates at different magnifications. As shown in FIG. 1 and FIG. 2, a large number of line traces, caused by both a lathe and a grinder, on the surface of the lathe-turned titanium substrate are observed.

Furthermore, as shown in FIG. 1, at a magnification of 1000:1, it was confirmed that the titanium substrate that was treated with 5M NaOH had a large number of micropores formed on the surface. Furthermore, these micropores were internally connected in a form of a net, like a sponge. The diameters of the micropores were in the range of a few scores of nm to approximately 100 nm.

Furthermore, as shown in FIG. 1, a large number of holes were also observed on the surface of the titanium substrate that was acid-etched, however, the diameters of these holes were considerably larger at several μm.

Whereas, as shown in FIG. 1, it was confirmed that a large number of convexities (projections/spikes/nano edges), a large number of concavities (crevasses/nano-holes/pores) were formed in the titanium substrate that was treated with 10M NaOH. Hence, a formation of a combination of large numbers of convexities and concavities was confirmed. A large number of crevasses existed in the concavities. It was confirmed that the groove-width of these grooves were of a nano scale. "Nano scale" indicates a range from greater or equal to 100 nm to less than 1,000 nm.

In regard to the crevasse-like grooves, a large number of grooves that are formed as cracks in the surface, the widths of which gradually narrow in the depth direction, were confirmed. The grooves penetrate the surface layer that is formed of sodium titanate, and either penetrate into the titanium layer therebelow or have a depth that occupies most of the depth of the surface layer.

Figure 3A:
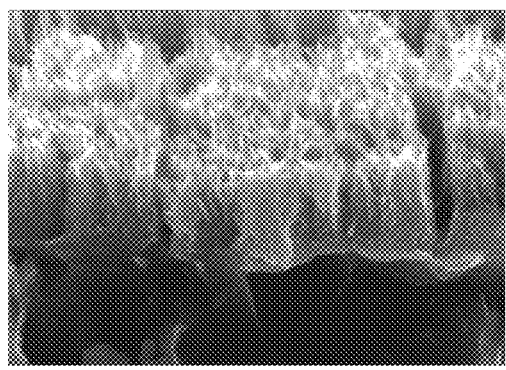
FIG. 3A shows an SEM photograph of a side sectional view of a titanium substrate that has been treated with 10M NaOH.
Figure 3B:
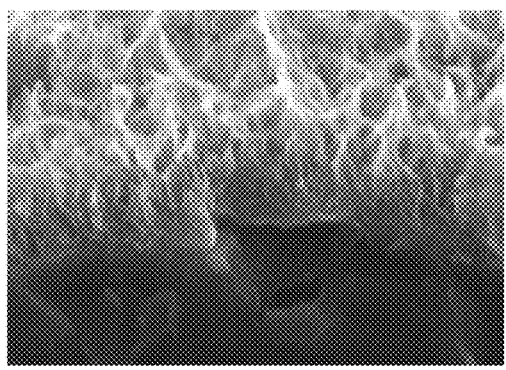
FIG. 3B shows an SEM photograph of a side sectional view of a titanium substrate that has been treated with 5M NaOH.
Figure 4A:
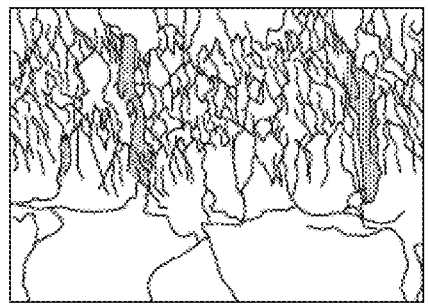
FIGS. 4A and 4B show partial schematic views of the SEM photographs shown in FIGS. 3A and 3B, respectively.
Figure 4B:
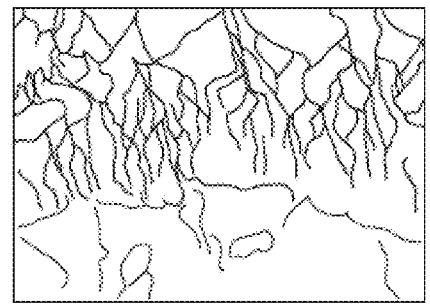
Figure 5A:
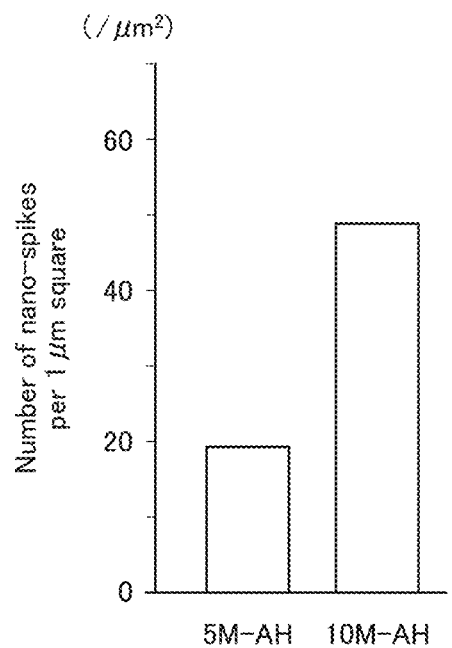
FIGS. 5A-5D are graphs showing the surface views of a titanium substrate that has been treated with 10M NaOH and a titanium substrate that has been treated with 5M NaOH.
Figure 5B:
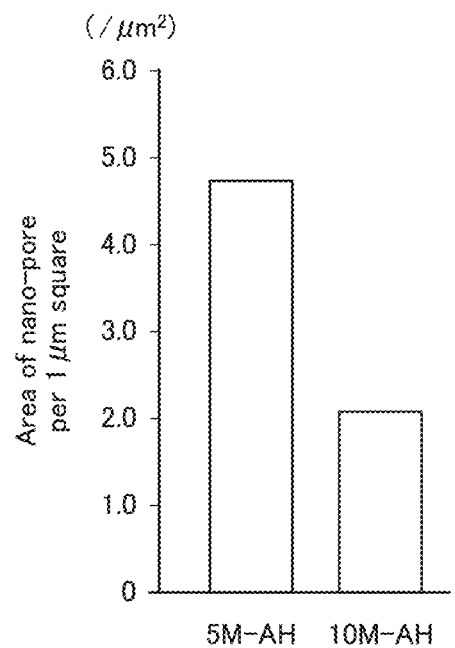
Figure 5C:
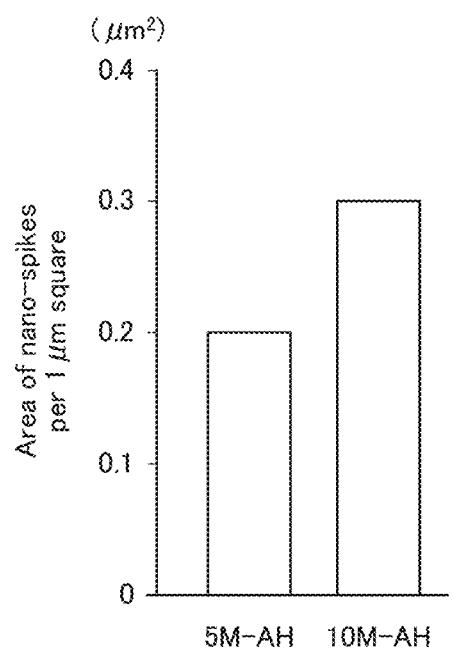
Figure 5D:
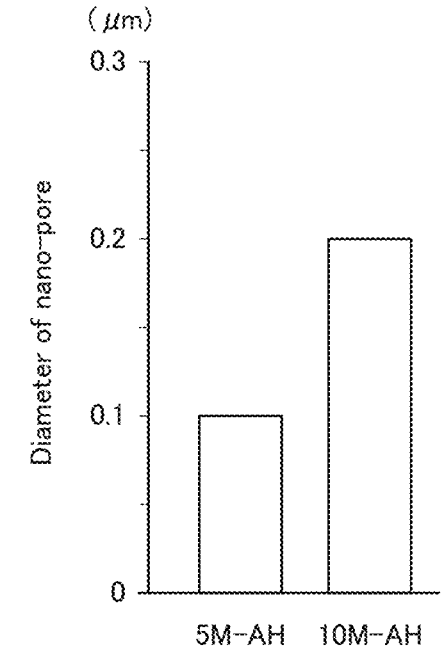

FIG. 3A shows an SEM photograph of a side sectional view of a titanium substrate that has been treated with 10M NaOH. FIG. 3B shows an SEM photograph of a side sectional view of a titanium substrate that has been treated with 5M NaOH. FIGS. 4A and 4B show partial schematic views of the SEM photographs shown in FIGS. 3A and 3B, respectively.

As can be understood by the side sectional views, crevasse-like grooves were observed in the titanium substrate that was treated with 10M NaOH; however, crevasse-like grooves were not observed in the titanium substrate that was treated with 5M NaOH, but rather round or oval micropores could be observed.

Furthermore, upon tests being carried out using an electron probe micro analyzer (EPMA), a surface layer that included the elements sodium, oxygen and titanium were observed in the surface of the titanium substrate.

As shown in FIG. 5, it was confirmed that the titanium substrate that was treated with 10M NaOH has approximately 2.5 times the number of projections and approximately 1.5 times the amount of area per 1 square μm compared to those of the titanium substrate that was treated with 5M NaOH. Furthermore, it was confirmed that the diameters of the grooves in the titanium substrate that was treated with 10M NaOH were approximately twice the size of those of the titanium substrate that was treated with 5M NaOH.

Figure 6A:
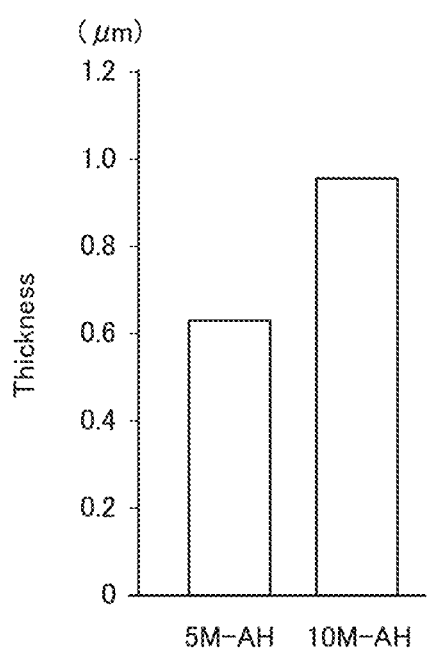
FIGS. 6A and 6B are graphs showing the surface views of a titanium substrate that has been treated with 10M NaOH and a titanium substrate that has been treated with 5M NaOH.
Figure 6B:
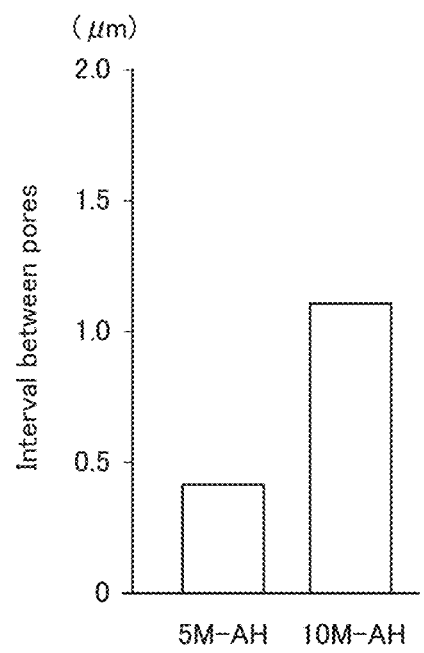

Furthermore, FIG. 6A shows the thicknesses of the upper surface layers of the titanium substrate that was treated with 10M NaOH and the titanium substrate that was treated with 5M NaOH; FIG. 6B shows the distances between the concavities (grooves) (Interval between pores).

As shown in FIG. 6A, it was confirmed that in the upper surface layer (the area at which the elements sodium, oxygen and titanium were detected by the EPMA), the titanium substrate treated with 10M NaOH is thicker than the titanium substrate treated with 5M NaOH. However, as shown in FIG. 6A, it was confirmed that even in the titanium substrate treated with 10M NaOH the layer thickness was less than 1 µm.

Furthermore, as shown in FIG. 6B, in the titanium substrate treated with 5M NaOH, the intervals between the concavities (nanopores) are approximately 0.5 µm, whereas in titanium substrate treated 10M NaOH, the intervals between the concavities (grooves (crevasses)) are approximately 1.0 µm.

Figure 7:
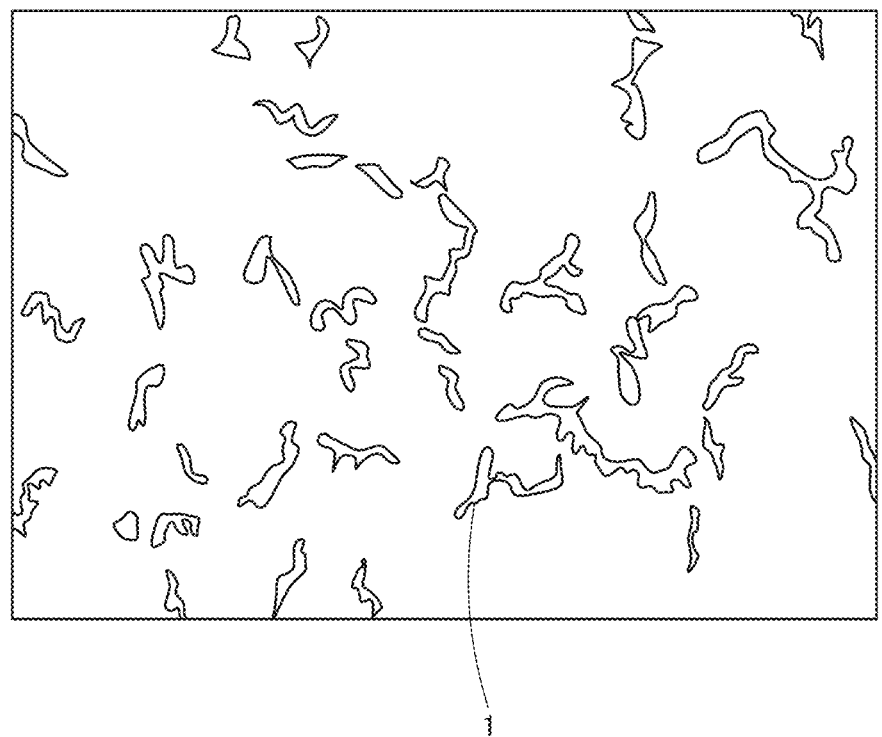
FIG. 7 is a partial schematic view of the surface of the titanium substrate, shown in FIG. 1, which has been treated with 10M NaOH.

FIG. 7 is a partial schematic view of the surface of the titanium substrate shown in FIG. 1, which has been treated with 10M NaOH. Some of the grooves that are observable by the naked eye are shown from the SEM photograph of the surface of the titanium substrate of FIG. 1, at a magnification of 1000:1.

As shown in FIG. 7, a large number of crevasse-like grooves 1 are formed on the surface of the titanium substrate which has been treated with 10M NaOH. The portions shown as white in the SEM photograph of FIG. 1 indicate high raised portions of a large height. As seen in the SEM photograph of FIG. 1, a large number of raised portions are observed. The projections also included long and thin interconnecting protrusions. The projections and grooves 1 of the protrusion structure can be respectively formed as singular long and narrow profile, or can be formed as a plurality of branches.

Figure 8:
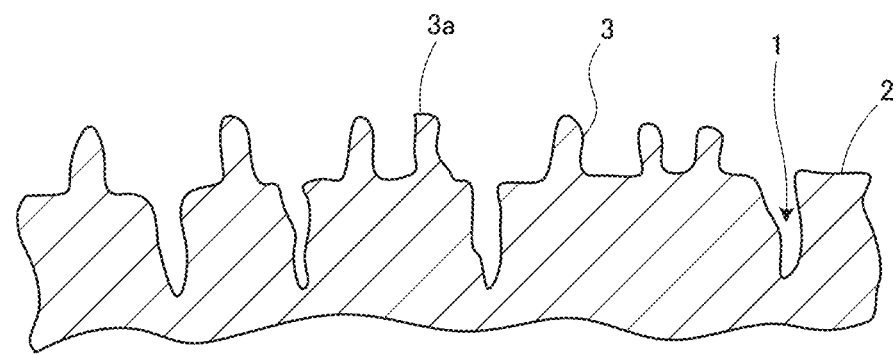
FIG. 8 is a partial schematic view of the side sectional view of the titanium substrate that has been treated with 10M NaOH.

FIG. 8 is a partial schematic view of the side sectional view of the titanium substrate that has been treated with 10M NaOH. As shown in FIG. 8, surface 2 includes the crevasse-like grooves 1, of a nano scale, and a plurality of projections 3; it can be confirmed that the surface of the ground titanium substrate has been modified.

As shown in FIG. 8, one or a plurality of the projections 3 can exist between grooves 1, or an area can exist that does not have any projections 3. The projections 3 are not condensed into one site, but are rather spread out over the entirety of the surface 2. It is ideal for the projections 3 to be arranged at regular and approximately constant intervals.

Micropores that are smaller than the grooves 1 or pores that are not crevasses can be provided on the surface 2 of the titanium substrate treated with 10M NaOH.

Figure 9:
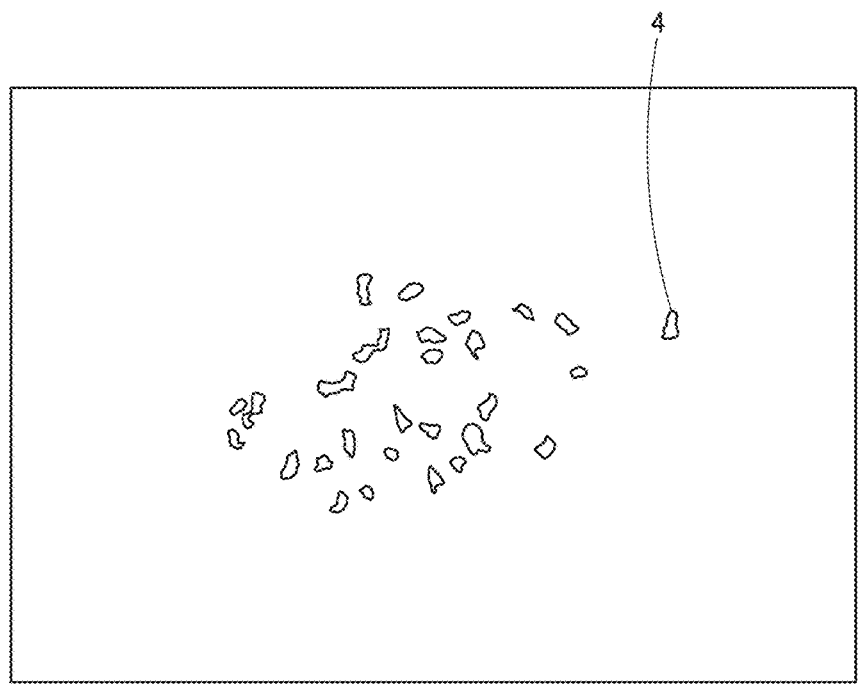
FIG. 9 is a partial schematic view of the surface of the titanium substrate, shown in FIG. 1, which has been treated with 5M NaOH.
Figure 10:
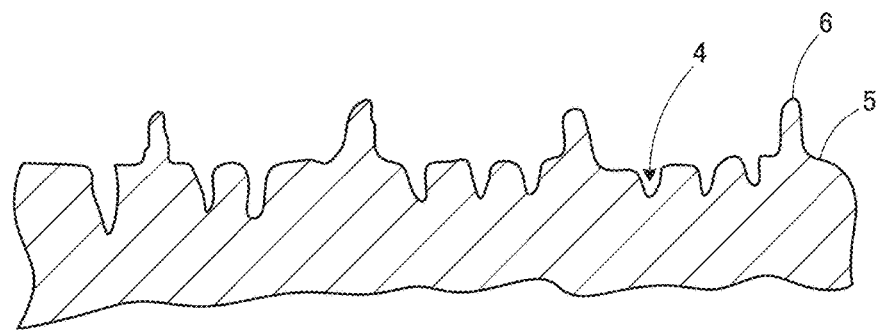
FIG. 10 is a partial schematic view of the side sectional view of the titanium substrate that has been treated with 5M NaOH.

FIG. 9 is a partial schematic view of the surface of the titanium substrate, shown in FIG. 1, which has been treated with 5M NaOH. FIG. 10 is a partial schematic view of the side sectional view of the titanium substrate that has been treated with 5M NaOH.

FIG. 9 shows some of the pores that are observable by the naked eye are shown from the SEM photograph of the surface of the titanium substrate of FIG. 1, at a magnification of 1000:1.

As shown in FIG. 9, a large number of micropores 4 formed on the surface of the titanium substrate treated with 5M NaOH can be confirmed. The micropores 4 are formed approximately circular or oval, and were not formed as crevasses. The diameters or widths of the micropores 4 are less than approximately 100 nm, confirming that these diameters/widths were smaller than the groove widths (indicating the width of the short side with respect to the aspect ratio) of the crevasse-like grooves 1 shown in FIG. 7.

Furthermore, as shown in FIG. 10, the depths of the micropores 4 were smaller than the depths of the grooves 1.

As shown in FIG. 10, a large number of projections 6 were observed on a surface 5 of the titanium substrate treated with 5M NaOH in addition to the large number of micropores 4.

The state of the surface modification of the titanium substrate treated with 10M NaOH and the state of the surface modification of the titanium substrate treated with 5M NaOH using the following parameters are shown in Table 1.

TABLE 1

|  | 5M NaOH | 10M NaOH |
| --- | --- | --- |
| No. of Projections per 1 square µm (µm$^2$) | 19.11(3.36) | 48.67(9.176) |
| Area of Projections per 1 square µm (µm$^2$) | 0.23(0.021) | 0.32(0.048) |
| Layer Thickness (µm) | 0.63(0.095) | 0.95(0.053) |
| No. of Grooves (Pores) (/µm) | 4.67(0.577) | 2(1) |
| Groove Width (Diameter of Pores) (µm) | 0.1(0.031) | 0.19(0.056) |
| Width between Grooves (Width between Pores) (µm) | 0.35(0.094) | 1.07(0.624) |
| Ra (within a square of 120 µm) (µm) | 0.13(0.006) | 0.35(0.031) |
| Rz (within a square of 120 µm) (µm) | 1.25(0.165) | 2.98(0.348) |
| Rsm (within a square of 120 µm) (µm) | 1.49(0.066) | 1.81(0.166) |

The parameters indicate average values. The numbers within brackets indicate the standard deviation (SD).

The area of projections indicated in Table 1 refers to the area as viewed from directly above the surface of the titanium substrate, i.e., the white portions in the SEM photograph in FIG. 1, and using FIG. 8 as an example, mainly corresponds to the total area of the spiked surfaces 3a of the projections 3.

Furthermore, the layer thickness in Table 1 refers to the thickness of the upper layer of the titanium substrate, and in the present test example corresponds to the layer thickness of the sodium titanate layer.

Furthermore, the groove width indicates the width of the short side of the aspect ratio of the crevasse-like grooves 1 shown in FIG. 7. Furthermore, the width of the short side is measured even in the case of the pores having a long and narrow oval profile, etc. The width between grooves (width between concavities) indicates the average interval between adjacent grooves (concavities).

Ra is the arithmetic roughness average, and Rz is the average roughness out of ten points. Rsm is the average of the length Xs of the profile-curve elements of a standard length (JIS B0601). The "profile-curve elements" refers to a curved portion formed by crests and adjacent roots, and the "length Xs of the profile curve elements" refers to the length of the line segment in the X-axis cut out by the profile curve elements (JIS B0601).

As indicated in Table 1, the number of projections, the area of projections, the layer thickness, the groove width, the width between grooves, Ra, Rz and Rsm of the titanium substrate treated with 10M NaOH are all greater than those of the titanium substrate treated with 5M NaOH.

In other words, it is confirmed that the titanium substrate treated with 10M NaOH has crevasse-like grooves having a wider groove width, more projections, and a greater surface undulation compared to the titanium substrate treated with 5M NaOH.

The above-described titanium substrate treated with 10M NaOH has had an effective surface modification carried out thereon for sealing soft tissue compared to the titanium substrate treated with 5M NaOH. In other words, the titanium substrate treated with 10M NaOH corresponds to the Present Example, and the titanium substrate treated with 5M NaOH correspond to the Comparative Example. Furthermore, the following descriptions will be given with the lathe-turned titanium substrate as Conventional Example 1 and the acid-etched titanium substrate as Conventional Example 2.

Figure 11:
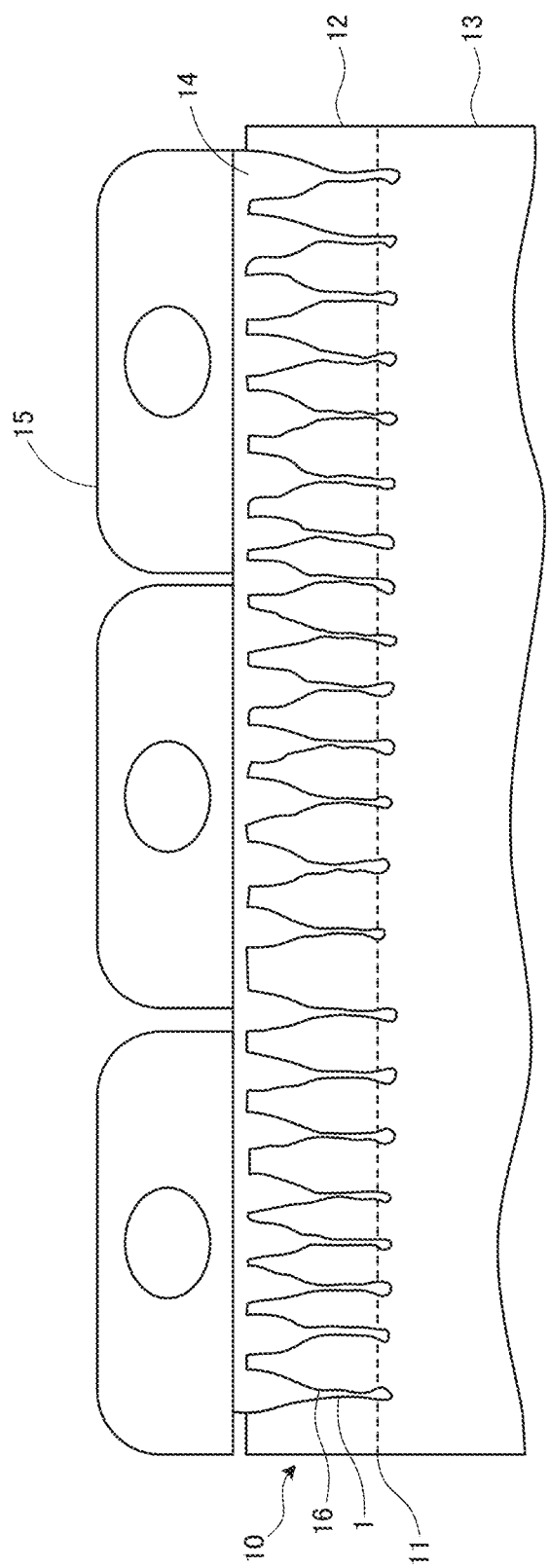
FIG. 11 is a schematic view showing an adhesion state between an implant body (Present Example), which is provided with a titanium substrate that is treated with 10M NaOH, and connective tissue.

FIG. 11 is a schematic view showing an adhesion state between an implant body (Present Example), which is provided with a titanium substrate that is treated with 10M NaOH, and connective tissue.

The implant body 10 shown in FIG. 11 is provided with a titanium substrate 11, and a sodium titanate layer 12 is formed on the upper surface layer of the titanium substrate 11 by the titanium substrate 11 being treated with 10M NaOH. Hence, the composition gradationally changes from a titanium layer 13 positioned at a surface internal portion to the sodium titanate layer 12. Although in FIG. 11 a boundary between the sodium titanate layer 12 and the titanium layer 13 is shown by a dotted line, these layers are not clearly divided and indicates the gradational change in the composition.

According to the example shown in FIG. 11, it is understood that the projections 3 (see FIG. 8) enhance the formation of gingival fibroblast focal adhesion 14 and the arrangement of a cell cytoskeleton 15. Accordingly, the cell adhesion strength is improved and the intracellular signal transduction pathway starting from the cell cytoskeleton 15 is activated, thereupon resulting in improvement in the manifestation of gingival collagen fiber production.

Furthermore, it is understood that the produced collagen fibers 16 entangle with the large number of projections 3 (see FIG. 8) and enter into the crevasse-like grooves 1. The collagen fibers 16 enter in from the grooves 1 until the titanium layer 13 position in the surface internal portion so that a Sharpey's fiber structure is formed on the implant surface. It is understood that in the Present Example the collagen fibers 16 can be arrangement in a fixed direction (in a direction substantially orthogonal to the implant surface).

In addition, in the Present Example, as shown in FIG. 8, the plurality of projections 3 are not concentrated at one location, but are arranged at regular intervals. Accordingly, cellular extension and cellular proliferation are promoted, and exceeding the general cell biological rule that says "cell differentiation capacity and cell proliferation capability have an inverse proportional relationship", it is concluded that both the matrix production was improved while maintaining the cell proliferation capability.

Figure 12:
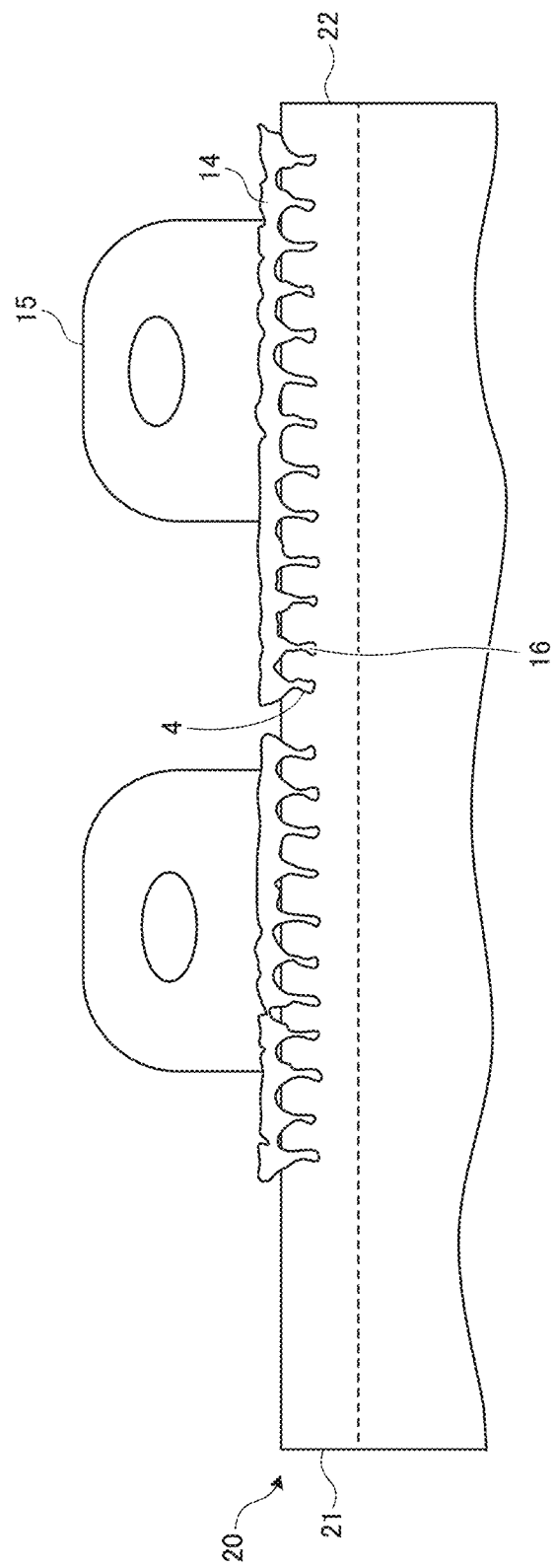
FIG. 12 is a schematic view showing an adhesion state between an implant body (Comparative Example), which is provided with a titanium substrate that is treated with 5M NaOH, and connective tissue.

FIG. 12 is a schematic view showing an adhesion state between an implant body (Comparative Example), which is provided with a titanium substrate that is treated with 5M NaOH, and connective tissue.

Similar to FIG. 11, an implant body 20 of the Comparative Example shown in FIG. 12 also has a sodium titanate layer 22 formed on a surface of a titanium substrate, however, the thickness thereof is thinner compared to that of the Present Example of FIG. 11.

In the Comparative Example shown in FIG. 12, the forming capability of the focal adhesion 14 and the arranging ability of the cell cytoskeleton 15 are weaker compared to the Present Example of FIG. 11; accordingly, the cell adhesion strength is low, and the manifestation of gingival collagen fiber production is low. Furthermore, in the Comparative Example of FIG. 12, crevasse-like grooves like those in the Present Example are not formed, only micropores 4 (see FIG. 9) of less than approximately 100 nm are formed; hence, it is concluded that the amount of the collagen fibers 16 that enter into the surface internal portion is small.

As shown in Table 1 above, the Present Example in which the 10M NaOH treatment is carried out results in larger values for the number of projections per 1 square μm, the area of projections per 1 square μm and Ra than in the Comparative Example in which the 5M NaOH treatment is carried out. Accordingly, in the Present Example, compared to the Comparative Example, the cell adhesive strength is improved and entanglement of the produced collagen fibers starts to occur. Furthermore, since the groove widths (pore diameter) of the grooves of the Present Example are larger compared to those of the Comparative Example, it is easier for the grown collagen fibers to be inserted further into the grooves. Furthermore, since Rsm is greater in the Present Example than in the Comparative Example, the matrix production capability of the gingival fibroblastic cells remains improved while further enhancing cellular extension and cellular proliferation.

Accordingly, in the Present Example, an adhesion effect between connective tissue and the implant surface can be achieved, and the soft tissue sealablity can be improved.

Furthermore, the crevasse-like grooves 1 provided in the Present Example are larger than the diameters of the collagen fibers, however, since the crevasse-like grooves 1 are smaller than typical oral bacteria, gingival fibers or Sharpey's fibers, configured of collagen fibers produced by fibroblastic adhesion and cell production, can penetrate and adhere while not increasing the susceptibility of bacterial infection.

Hence, in the Present Example, surface modification for soft tissue sealing has been carried out. The following parameters are desirable for the Present Example; namely, with respect to an SEM image, the average number of projections occupying 1 square μm being 20 through 60; the average area of the projections occupying 1 square μm being 0.25 μm$^2$ through 0.4 μm$^2$; the average groove width of the crevasse-like grooves being 0.15 μm through 0.30 μm; the average value of Ra in a 120 square μm being 0.15 μm through 0.50 μm; and the average value of Rsm in a 120 square μm being 1.50 μm through 3.00 μm.

In addition, it is desirable for the layer thickness of the sodium titanate layer to be within a range of 0.65 μm through 1.00 μm. Furthermore, it is desirable for the number of grooves occupying 1 square μm to be within a range of 1 through 4. Furthermore, it is desirable for the groove width to be within a range of 0.4 μm through 1.1 μm. Furthermore, it is desirable for Rz in 120 square μm to be within a range of 1.3 μm through 3.1 μm.

Thereafter, a confirmation test was carried out using the titanium substrates in each of the Present Example (10M-AH), the Comparative Example (5M-AH), Conventional Example 1 (TU) and Conventional Example 2 (AE).

Figures 13A, 13B, 13C:
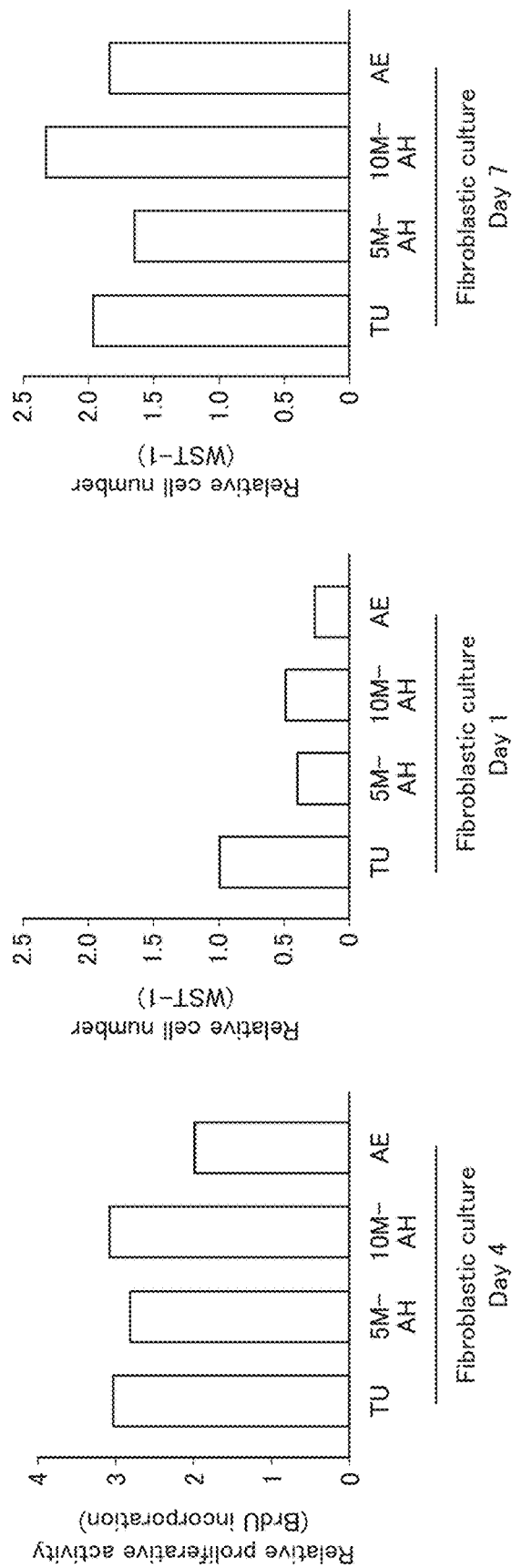
FIG. 13A is a "Day 4" graph which relatively compares the fibroblastic proliferation activity with respect to each titanium substrate of Conventional Example 1 (TU), Comparative Example (5M-AH), Present Example (10M-AH) and Conventional Example 2 (AE).
FIG. 13B is a "Day 1" graph which relatively compares the number of fibroblastic cells with respect to each titanium substrate.
FIG. 13C is a "Day 7" graph which relatively compares the number of fibroblastic cells with respect to each titanium substrate.

FIG. 13A is a "Day 4" graph which relatively compares the fibroblastic proliferation activity with respect to each titanium substrate of Conventional Example 1 (TU), Comparative Example (5M-AH), Present Example (10M-AH) and Conventional Example 2 (AE).

In the tests, the BrdU incorporation is relatively compared as a cell proliferation indicator for "Day 4". As shown in FIG. 13A, Conventional Example 2 (AE) had the lowest BrdU incorporation out of all the titanium substrates.

FIG. 13B is a "Day 1" graph which relatively compares the number of fibroblastic cells with respect to each titanium substrate. FIG. 13C is a "Day 7" graph which relatively compares the number of fibroblastic cells with respect to each titanium substrate.

In FIG. 13B and FIG. 13C, cell proliferation was assessed using a dye method (WST-1). As shown in FIG. 13B, on the first day, Conventional Example 1 (TU) had the largest number of cells; and the Present Example (10M-AH), the Comparative Example (5M-AH) and Conventional Example 2 (AE) each had less than 50% of the number in Conventional Example 1 (TU). However, on the seventh day, it was confirmed that the Present Example (10M-AH) had the greatest number of cells.

Figure 14:
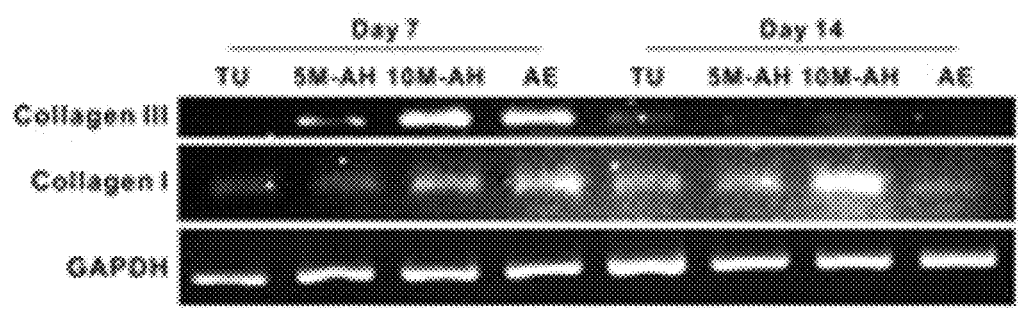
FIG. 14 shows a visualization of the experimental results of the gene findings in each titanium substrate of Conventional Example 1 (TU), Comparative Example (5M-AH), Present Example (10M-AH) and Conventional Example 2 (AE).
Figure 15:
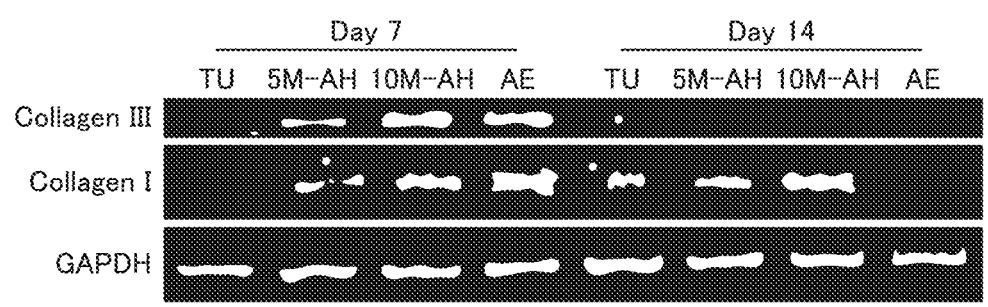
FIG. 15 shows a partial schematic view of FIG. 14.

FIG. 14 shows a visualization of the experimental results of the gene findings in each titanium substrate of Conventional Example 1 (TU), Comparative Example (5M-AH), Present Example (10M-AH) and Conventional Example 2 (AE). FIG. 15 shows a partial schematic view of FIG. 14.

The experimental method used was to, in a culture test, extract messenger RNA from the seventh day and the fourteenth day upon semination of gingival fibroblastic cells, and convert the messenger RNA into DNA using reverse transcriptase. Thereafter, the base sequence portions corresponding to each collagen were amplified using a polymerase chain reaction, and were visualized by electrophoresis. In the experiment collagen I and collagen III were used. Collagen I is a collagen that exists in the largest amounts invertebrates, and produces strength in the gingiva. Collagen III cultivates at the initial stage of the wound healing process, and it is said that healing progresses by being substituted with collagen I.

The experiment shown in FIG. 14 indicates a stronger light as the genetic expression is more active. As shown in FIG. 14 and FIG. 15, in the Present Example (10M-AH) it was confirmed that light of collagen I manifested both on the seventh day and on the fourteenth day. Also, in the Present Example (10M-AH), it was confirmed that collagen III manifested on the seventh day. Whereas, in the Comparative Example (5M-AH), it was confirmed that collagen I did not manifest very strongly on the seventh day or on the fourteenth day. Furthermore, in Conventional Example 2 (AE), it was confirmed that collagen I and collagen III manifested on the seventh day in the same manner as the Present Example (10M-AH), however, both disappeared on the fourteenth day.

Figure 16A:
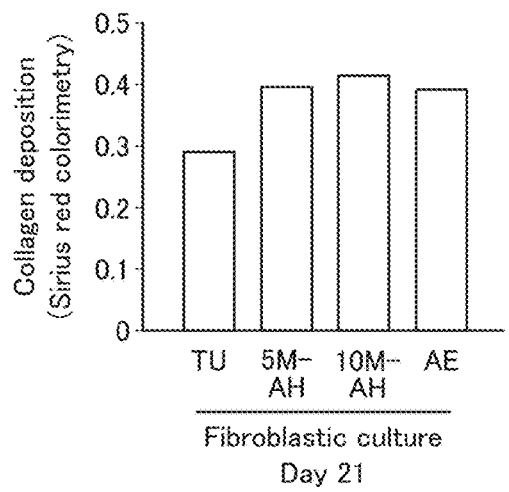
FIG. 16A is a graph showing the amount of collagen fibers on the surfaces of each titanium substrate of Conventional Example 1 (TU), Comparative Example (5M-AH), Present Example (10M-AH) and Conventional Example 2 (AE).
Figure 16B:
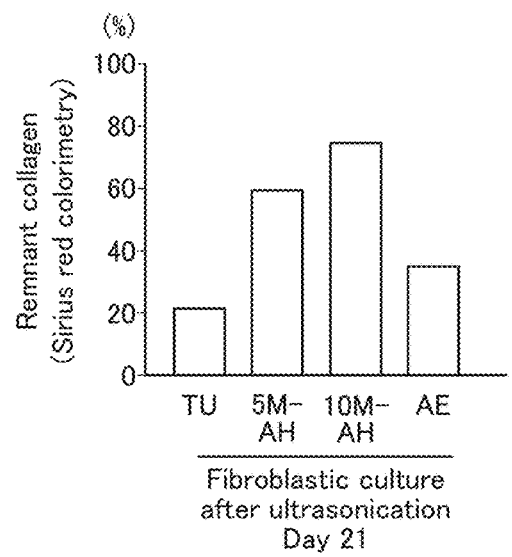
FIG. 16B is a graph showing the amount of collagen fibers after an ultrasonication process is carried out on each titanium substrate.
Figure 16C:
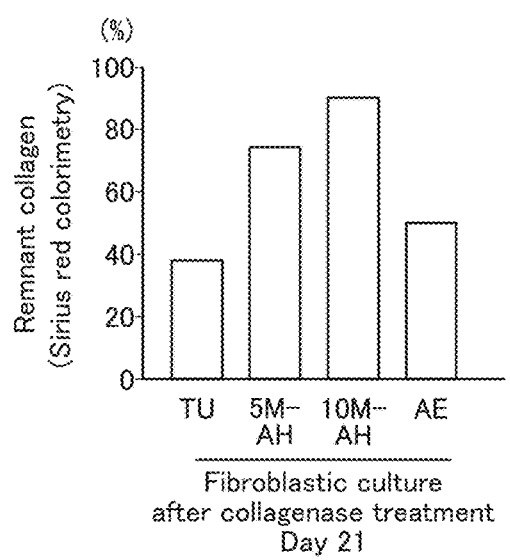
FIG. 16C is a graph showing the amount of collagen fibers after collagenase (enzymes) is added to each titanium substrate.

FIG. 16A shows the amount of collagen fibers on the surfaces of each titanium substrate of Conventional Example 1 (TU), Comparative Example (5M-AH), Present Example (10M-AH) and Conventional Example 2 (AE); FIG. 16B shows the amount of collagen fibers after an ultrasonication process is carried out on each titanium substrate; and FIG. 16C shows the amount of collagen fibers after collagenase (enzymes) is added to each titanium substrate.

FIG. 16A shows the amount of collagen fibers on the twenty first day. In the experiment, a portion that is dyed red is observed with a bright field microscope, and the amount of collagen fibers is calculated from the area of the dyed portion.

As shown in FIG. 16A, the amount of collagen fibers of the Present Example (10M-AH), the Comparative Example (5M-AH) and Conventional Example 2 (AE) were substantially the same. Furthermore, it was confirmed that the amount of collagen fibers of the Present Example (10M-AH), the Comparative Example (5M-AH) and Conventional Example 2 (AE) are 1.3 times the amount of collagen fibers of Conventional Example 1 (TU).

As shown in FIG. 16B, it was confirmed that upon carrying out ultrasonication on each titanium substrate on the twenty first day shown in FIG. 16A, 60% or more of the amount of collagen fibers of the Present Example (10M-AH) and of the Comparative Example (5M-AH) remained. Furthermore, it was confirmed that the Present Example (10M-AH) had the most remaining amount of collagen fibers compared to the Comparative Example (5M-AH), Conventional Example 1 (TU) and Conventional Example 2 (AE). It was confirmed that the amount of collagen fibers of the Present Example shown in FIG. 16B was about four times that of Conventional Example 1, twice that of Conventional Example 2, and 1.4 times that of the Comparative Example.

Furthermore, as shown in FIG. 16C, upon adding collagenase (enzymes) to each titanium substrate on the twenty first day shown in FIG. 16A, it was confirmed that approximately 90% of the amount of collagen fibers of the Present Example (10M-AH), and 70% of the amount of collagen fibers of the Comparative Example (5M-AH) remain. Furthermore, it was confirmed that the Present Example (10M-AH) had the most remaining amount of collagen fibers compared to the Comparative Example (5M-AH), Conventional Example 1 (TU) and Conventional Example 2 (AE). It was confirmed that the amount of collagen fibers of the Present Example shown in FIG. 16C was about twice that of Conventional Example 1, 1.7 times that of Conventional Example 2, and 1.2 times that of the Comparative Example.

Furthermore, upon treating each titanium substrate with hydrogen peroxide ($H_2O_2$) on the twenty first day, it was confirmed that the amount of collagen fibers in Conventional Example 1 (TU) and in Conventional Example 2 (AE) was 30% or less, whereas, the amount of collagen fibers of the Present Example (10M-AH) and the Comparative Example (5M-AH) was 50% or more.

Hence, in the Present Example (10M-AH), the adhesiveness of the connective tissue is higher compared to the Comparative Example (5M-AH), Conventional Example 1 (TU) and Conventional Example 2 (AE). In other words, in the Comparative Example (5M-AH), Conventional Example 1 (TU) and Conventional Example 2 (AE), it was confirmed that the connective tissue does not favorably adhere to the surface of the titanium substrate (the surface of the implant body), and the connective tissue easily peels away from the surface.

Figure 17A:
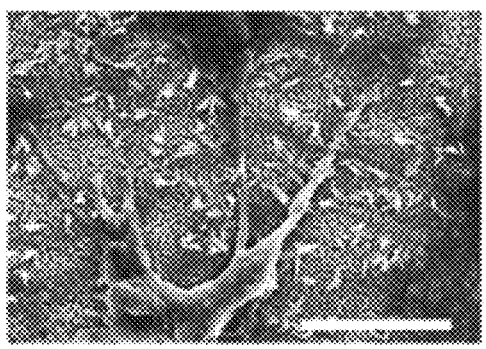
FIGS. 17A and 17B show SEM photographs showing surfaces states after collagenase is applied in FIG. 16C.
Figure 17B:
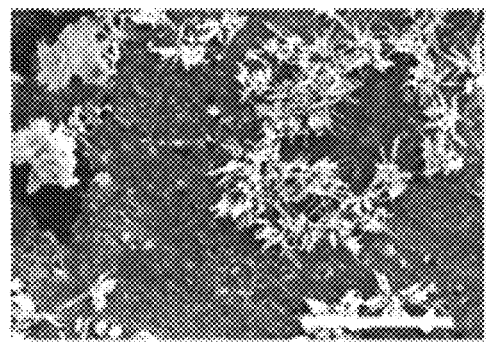
Figure 18A:
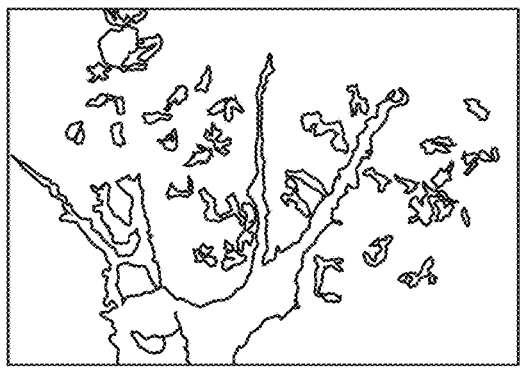
FIGS. 18A and 18B are partial schematic views showing the SEM photographs of FIGS. 17A and 17B, respectively.
Figure 18B:

FIG. 17 shows SEM photographs showing surface states after collagenase is applied in FIG. 16C. FIG. 17A is an SEM photograph of the titanium substrate of Comparative Example, and FIG. 17B is an SEM photograph of the titanium substrate of Present Example. FIGS. 18A and 18B are partial schematic views showing the SEM photographs of FIGS. 17A and 17B, respectively.

In the Present Example shown in FIG. 17B and FIG. 18B, it was confirmed that a large amount of collagen fibers (extracellular matrix; ECM) remain on the surface compared to the Comparative Example shown in FIG. 17A and FIG. 17B.

FIG. 19 shows graphs indicating the physical strength of each titanium substrate of Present Example (10M-AH) and Comparative Example (5M-AH).

Figure 19A:
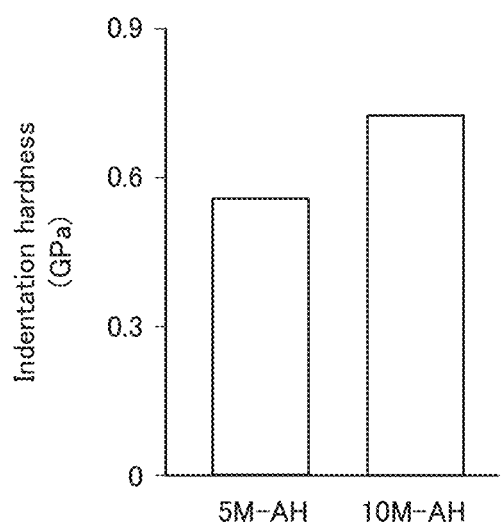
FIGS. 19A and 19B show graphs indicating the physical strength of each titanium substrate of Present Example (10M-AH) and Comparative Example (5M-AH).

FIG. 19A shows the experimental results of the indentation hardness of each titanium substrate of the Present Example (10M-AH) and the Comparative Example (5M-AH). Furthermore, FIG. 19B shows the experimental results of the indentation Young's modulus of each titanium substrate of the Present Example (10M-AH) and the Comparative Example (5M-AH).

Figure 19B:
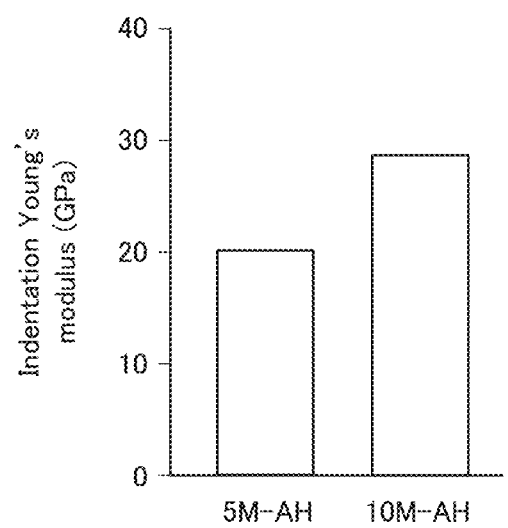

As shown in FIG. 19A and FIG. 19B, the indentation hardness and the indentation Young's modulus were both greater in the Present Example compared to the Comparative Example. Furthermore, the indentation hardness is approximately 0.72 GPa in the Present Example and approximately 0.56 GPa in the Comparative Example. In addition, the indentation Young's modulus in the Present Example is approximately 28.2 GPa and approximately 20.3 GPa in the Comparative Example.

In the present invention, the implant body can be formed from, e.g., a titanium alloy of titanium and aluminum. When titanium-aluminum is used as a titanium alloy, a sodium aluminum titanate layer is formed on the upper layer of the implant body.

Alternatively, the implant body can be formed from zirconia. In addition, the implant body can be formed from a new material which can be implanted into a living body. These materials also can achieve soft tissue sealablity by carrying out surface modification in which a plurality of projections and a plurality of crevasse-like nanoscale grooves are provided.

In the Present Example the NaOH concentration is set at 10M, and in the Comparative Example the NaOH concentration is set at 5M; accordingly, in the Present Example, the layer thickness is approximately 950 nm, which is approximately 200 nm thicker compared to that of the Comparative Example. Furthermore, in the Comparative Example, gaps were observed in the reticulated sodium titanate crystal structure formation, however, in the Present Example, it is concluded that such gaps shrink during immersion in sodium hydroxide solution so that the surface has a structure that is close to a flat plate. Furthermore, in regard to the crevasse-like grooves in the Present Example, it is concluded that nanoscale crevasses occurred as cracks in the surface due to the difference in the heat expansion coefficients between sodium titanate and the base metal of pure titanium during sintering.

Figure 20:
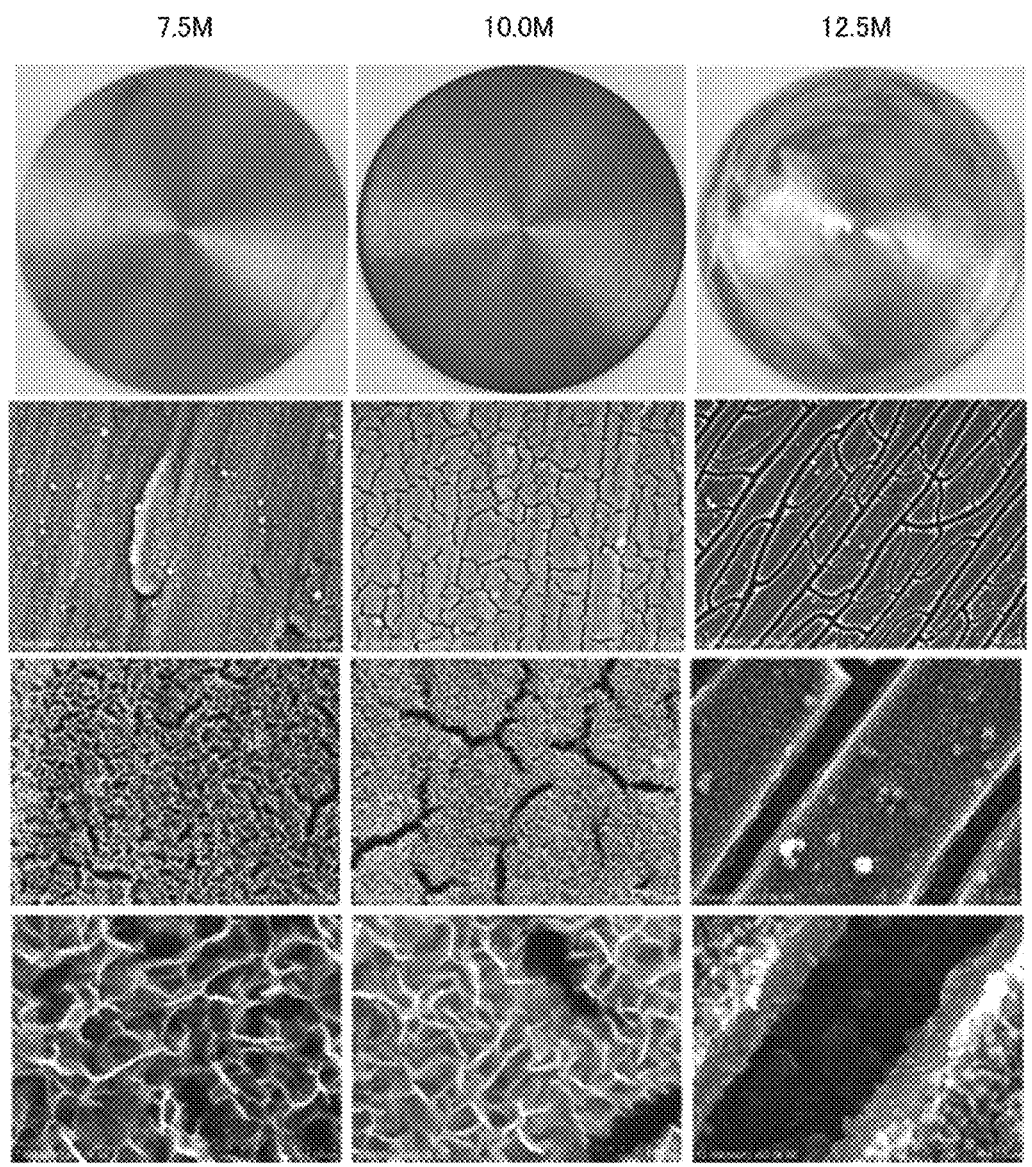
FIG. 20 shows photographs indicating the surface states of a titanium substrate treated with 7.5M NaOH, a titanium substrate treated with 10M NaOH, and a titanium substrate treated with 12.5M NaOH.
Figure 21:
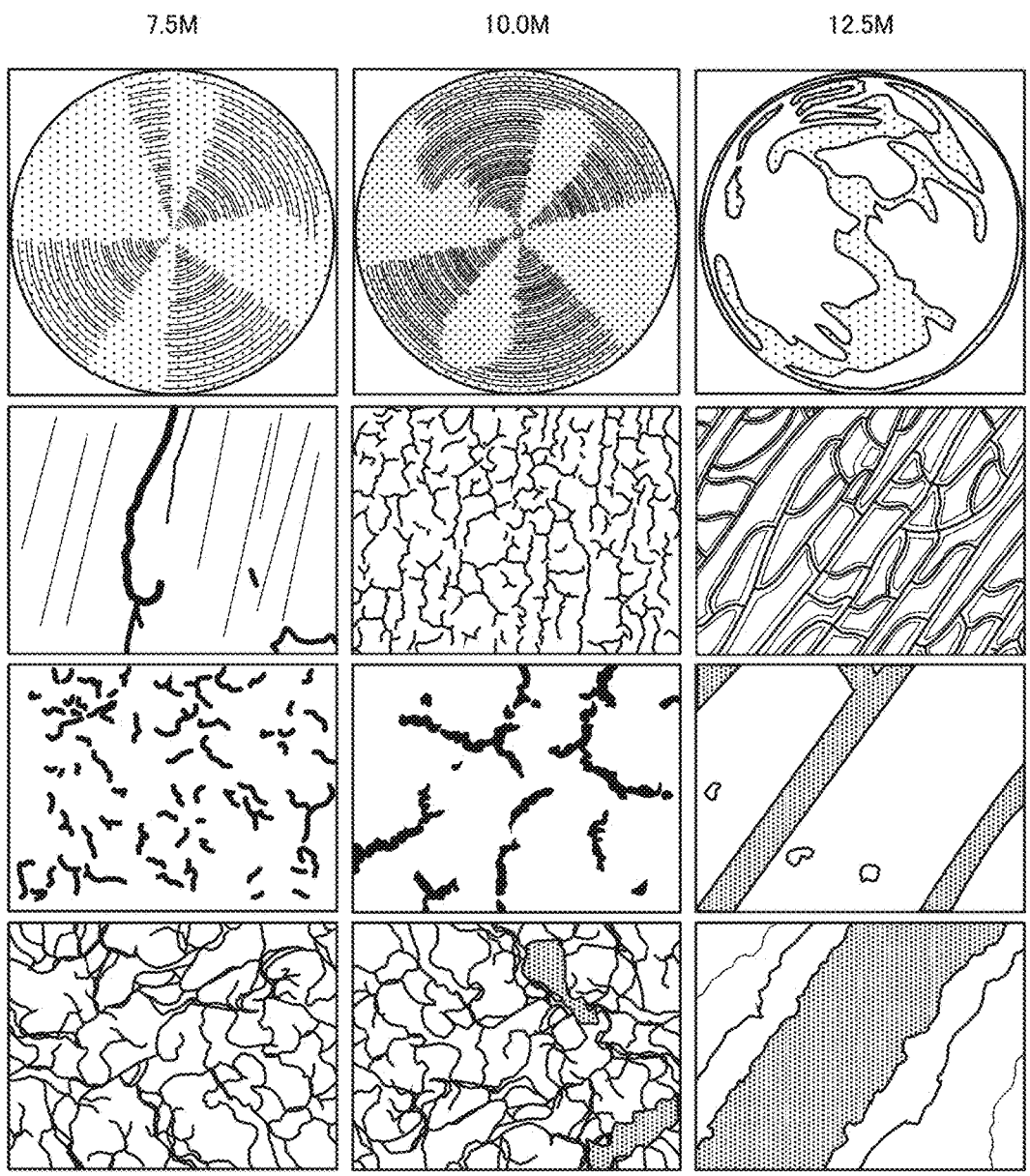
FIG. 21 shows partial schematic views of each photograph of FIG. 20.

FIG. 20 shows photographs indicating the surface states of a titanium substrate treated with 7.5M NaOH, a titanium substrate treated with 10M NaOH, and a titanium substrate treated with 12.5M NaOH. FIG. 21 shows partial schematic views of each photograph of FIG. 20.

Furthermore, the surface of a titanium substrate was modified under the same conditions as the above-described "C: 10M NaOH" (Present Example) except for the change in the concentration of the NaOH.

The first row of photographs from the top shown in FIG. 20 are photographs showing the entire surface of each titanium substrate, and the second through fourth rows of photographs are SEM photographs having differing magnifications.

As shown in FIG. 20 and FIG. 21, it was confirmed that the surface was modified to have a plurality of projections and a plurality of crevasse-like nanoscale grooves also in a case where the concentration of the NaOH is other than 10M, such as 7.5M and 12.5M. Furthermore, even if the concentration of the NaOH is increased to around 12.5, it was confirmed that crevasse-like grooves are formed having widths that do not allow bacteria to be entrapped therein.

The implant body can be applied to a dental implant. Accordingly, the implant body can achieve an effect of adhering to gingival connective tissue in addition to adhesion to the bone, thereby securing favorable soft tissue sealablity without increasing susceptibility of bacterial infection.

The implant body can also be applied to an implant other than a dental implant. In particular, according to the present invention, the implant body can be favorably applied for a use that requires enhancement of focal adhesion formation and cultivation of cell cytoskeleton, and enhancement of penetration of collagen fibers into the implant to effectively increase the adhesion strength with connective tissue.

Specifically, it is possible to apply the present invention to a skin-penetration endosseous implant (endosseous fastener) other than at the dental and oral mucosal region, or to various skin-penetration medical devices such as a gastrostoma, a tracheostomy insertion tube, artificial vocal cords, and an blood vessel indwelling needle, etc. (central venous nutrition indwelling needle, etc.). Accordingly, the present invention is applicable to a penetration implant that penetrates both the mucosa and the dermal tissue, thereby enhancing cell adhesion and focal adhesion formation in both the epidermis and the mucosal epithelium.

The present disclosure relates to subject matter contained in Japanese Patent Application No. 2014-031290 (filed on Feb. 21, 2014) which is expressly incorporated herein in its entirety.

The invention claimed is:

1. An implant body formed, said implant body comprising:
a modified surface, provided with a plurality of projections and a plurality of crevasse-like nanoscale grooves, by which focal adhesion formation, penetration of collagen fibers, arrangement of the collagen fibers in a single direction to thereby adhere to connective tissue, and soft tissue sealability are possible,
wherein, with respect to an SEM image, the average number of projections occupying a 1 µm square is 20 through 60, the average area of the projections occupying a 1 µm square is 0.25 m² through 0.40 m², and the average value of Ra in a 120 µm square is 0.15 µm through 0.50 m,
a titanium substrate, and
a surface layer that is formed of sodium titanate formed in the surface of the titanium substrate,
wherein the layer thickness of the surface layer is within a range of 0.65 µm through 1.00 µm,
wherein the grooves penetrate the surface layer, and penetrate into the titanium substrate, and
wherein grooves are configured so that the collagen fibers can enter into the grooves from the surface layer and into the titanium substrate.

2. The implant body according to claim 1, wherein said implant body can be applied to a penetration implant that penetrates both the mucosa and the dermal tissue.

* * * * *